(12) United States Patent
Guo

(10) Patent No.: US 11,136,546 B2
(45) Date of Patent: Oct. 5, 2021

(54) **RECOMBINANT *ESCHERICHIA COLI* AND APPLICATION OF THE SAME**

(71) Applicant: Zhengzhou Zhonghao Biological Technology Co., Ltd., Zhengzhou (CN)

(72) Inventor: Liangxing Guo, Zhengzhou (CN)

(73) Assignee: ZHENGZHOU ZHONGHAO BIOLOGICAL TECHNOLOGY CO., LTD., Xingyang (CN)

( * ) Notice: Subject to any disclaimer, the term of this patent is extended or adjusted under 35 U.S.C. 154(b) by 280 days.

(21) Appl. No.: 16/354,304

(22) Filed: Mar. 15, 2019

(65) Prior Publication Data

US 2020/0165690 A1 May 28, 2020

(30) Foreign Application Priority Data

Nov. 22, 2018 (CN) .......................... 201811398631.8

(51) Int. Cl.
  *C12N 15/00* (2006.01)
  *C12P 7/46* (2006.01)
  *C12N 1/20* (2006.01)
  *C12R 1/19* (2006.01)

(52) U.S. Cl.
  CPC ................ *C12N 1/205* (2021.05); *C12P 7/46* (2013.01); *C12R 2001/19* (2021.05)

(58) Field of Classification Search
  CPC .. C12N 15/70; C12N 2800/10; C07K 14/245; C07K 14/195; C12P 7/46; C12P 21/02; C12R 1/19
  USPC .................. 435/252.33, 34, 32, 252.1, 320.1
  See application file for complete search history.

(56) References Cited

PUBLICATIONS

Mukhupadhyay et al., 2004, 14, pp. 739-751.*

* cited by examiner

*Primary Examiner* — Robert B Mondesi
*Assistant Examiner* — Mohammad Y Meah
(74) *Attorney, Agent, or Firm* — The Roy Gross Law Firm, LLC; Roy Gross

(57) ABSTRACT

Disclosed in the present invention is a recombinant *Escherichia coli* and application thereof. The recombinant *Escherichia coli* was deposited on Aug. 28, 2018 in the China General Microbiological Culture Collection Center with the preservation number CGMCC No. 16349. The recombinant *Escherichia coli* is fermented and cultured, and the concentration of Microcin J25 in the supernatant can reach 4000 mg/L or more.

2 Claims, 1 Drawing Sheet
Specification includes a Sequence Listing.

SEQUENCE LISTING

```
<160> NUMBER OF SEQ ID NOS: 4

<210> SEQ ID NO 1
<211> LENGTH: 4089
<212> TYPE: DNA
<213> ORGANISM: Escherichia coli
<220> FEATURE:
<223> OTHER INFORMATION: mcjABCD

<400> SEQUENCE: 1
atgattaagc attttcattt taataaactg tcttctggta aaaaaaataa tgttccatct      60
cctgcaaagg gggttataca aataaaaaaa tcagcatcgc aactcacaaa aggtggtgca     120
ggacatgtgc ctgagtattt tgtggggatt ggtacaccta tatctttcta tggctgaatg    180
atccgttact gcttaaccag ttatagagag gatcttgtta tcctggatat aattaatgat    240
agtttcagca tagtgcctga cgcaggtagc ttgctaaaag aaagagataa attgcttaaa    300
gaattcccac aactatctta ctttttttgac agtgaatatc atattggaag tgtttctcgt    360
aatagtgaca cttctttttct tgaagaacgc tggtttctac cagaacctga caaaacatta    420
tataagtgtt ctctatttaa acgatttata ttattactca aagtcttta ctatagctgg      480 aatattgaaa aaaaagggat ggcatggatt ttcataagta ataaaaaaga gaataggcta    540
tactccttga atgaagagca tcttatccgg aaagaaatta gtaatctttc cattatcttt    600
catcttaata tttttaaatc tgactgtctt acctattcat acgcactaaa aagaattctt    660
aattccagaa atattgatgc tcatcttgtt attggtgtaa ggacacaacc tttttatagc    720
cactcttggg tggaggttgg gggacaagtt atcaatgatg ctcccaatat gcgggataaa    780
ttatctgtta ttgcagagat atagatggaa atatttaatg tcaagttaaa tgatacttca    840
attagaatta ttttctgtaa aacgctttct gccttccgga cagaaaatac catcgttatg    900
ctcaaaggaa aagcagtttc aaatggcaaa cctgtatcca cagaggagat tgccagagta    960
gtggaagaaa aggtgtttc agaagtaata gaaaatttag atggtgtttt ctgtatccta    1020
atttatcatt ttaatgatct ccttataggg aaaagcattc aatcaggccc cgctctattt   1080
tattgtaaaa agaatatgga tattttttgtt tcggataaaa tttctgatat caaatttttg    1140
aatccagata tgacattcag tctaaatata aaaatggcag aacattatct gtcaggaaat     1200
cgaatagcaa cccaggaatc actaatcact ggcatttaca aagtaaataa tggtgagttt     1260
```

```
ataaaattta ataatcagtt gaaacctgtg ctacttcgtg atgagtttag tattaccaaa    1320
aagaacaatt caactatcga cagtatcatt gataatattg agatgatgcg ggataataga    1380
aaaatagccc tattattctc cggaggattg gattctgcat taatttttca cacacttaaa    1440
gaatcaggta acaaattctg cgcttatcat ttttttttctg atgaatctga tgacagtgaa    1500
aagtattttg ctaaggaata ctgttcaaaa tatggagttg attttatatc tgttaataaa    1560
aacatcaact ttaatgaaaa actttatttc aatttaaatc ctaatagtcc ggacgaaatc    1620
cctttgatat ttgaacagac agatgaagaa ggtgaaggtc agccccccat agacgatgat    1680
ttattatatc tatgtggtca cggtggagat catattttcg acaaaatcc ttcagaactt     1740 tttggcattg atgcatatcg aagtcatggc ttgatgttta tgcataaaaa aatagtagaa    1800
ttttccaatc tcagggaaa gagatataaa gatatccat ttttcaaatat ttccgcattc     1860 attaatacat ccaacggatg ttctccagca aagcaagagc acgtatcaga tatgaaactt    1920
gcctctgctc agttttttgc aactgattat acaggaaaaa ttaataaact aactccattc    1980
ctgcataaaa atattatcca gcattatgct ggcttaccag ttttttagtct atttaaccag    2040 cactttgatc gttatcccgt tcgttatgaa gcgtttcaac gatttggttc agatattttc    2100
tggaaaaaaa ccaaacggtc atcttcacag ctaatattca gaattctatc cggtaaaaag    2160
gatgaactag tgaatacaat aaaacagtca ggattaattg aaatattagg cattaaccat    2220
attgaattag aaagcatttt gtatgaaaat acgactacac gtctgacaac ggaactacca    2280
tatatactta acttataccg tctggcaaaa ttcattcaac ttcaatccat tgattataaa    2340
ggttaaatgg aaagaaaaca gaaaaactca ttatttaatt atatttattc attaatggat    2400
gcaagaggta aatttttatt cttttccatg ttattcatta catcattatc atcgataatc    2460
atatctattt caccattgat tcttgcaaag attacagatt tactgtctgg ctcattgtca    2520
aattttagtt atgaatatct ggttttactt gcctgtttat acatgttttg cgttatatct    2580
aataaagcaa gtgttttttt atttatgata ctgcaaagta gtctacgtat taacatgcag    2640
aaaaaaatgt cgctaaaata tttgagagaa ttgtataacg aaaatataac taacttgagt    2700
aaaaataatg ctggatatac aacgcaaagt cttaaccagg cttcaaatga catttatatt    2760
cttgtgagaa atgtttccca gaatatcctg tcacctgtta taacttat ttctactatt      2820 gttgttgttt tatctacgaa ggactggttt tctgccggtg tgttttttct ctatattctg    2880
gtatttgtaa tttttaatac cagactgact ggcagtttag cgtcactcag aaaacacagc    2940
atggatatca ctcttaactc ttatagtctg ttatctgata ctgttgataa catgatagca    3000
gctaaaaaga taatgcatt aagacttatt tctgaacgtt atgaagatgc tctcactcag    3060
gaaaacaatg ctcagaaaaa atactggtta ctcagttcta agttcttttt attgaactct    3120
ttacttgctg taatattatt tggttctgta ttcatatata atatttttagg tgtgctgaat    3180 ggtgtagtta gtatcggcca cttcattatg attacatcat atatcattct tctttcaacg    3240
ccagtggaaa atataggggc attgctaagt gagatcaggc agtcaatgtc tagcctggca    3300
ggttttattc aacgtcatgc cgagaataaa gccacatctc cttcaatacc ttttctcaac    3360
atggagcgaa aattaaacct gtccataaga gagctttcat ttagctatag tgatgataaa    3420
aaaatactta attcagtcag tcttgacctt ttaccggaa aaatgtattc attaaccgga     3480
cccagtggtt caggaaaatc cacccttgta aaaataatat caggttacta taaaaattac    3540
tttggagaca tttatctgaa tgatatatcc ttacgtaata tcagtgatga ggatttgaat    3600
```

```
gatgctattt actacctaac acaagatgat tatatttta tggatacact acgatttaat    3660
ctccggctcg caaattacga cgcgtcagaa aatgaaatgt ttaaagttct taaactggca    3720
aatctttctg tcgtcaacaa tgaaccagtg agtctggata cacaccttat aaacagaggc    3780
aataactatt caggagggca aaaacaacga atttcgttag cgcgactgtt tttgagaaaa    3840
cctgcaataa ttattattga tgaagccaca tcggctctgg attatattaa tgaatcagaa    3900
attttatcat caataagaac tcattttcct gatgcgttaa ttataaatat tagtcaccga    3960
ataaatcttc tggagtgttc cgattgtgtt tatgtattga atgaaggaaa tattgttgct    4020
tctggccatt tcagggattt gatggtcagc aatgaataca tatcgggact ggcttctgtt    4080
actgaataa                                                           4089

<210> SEQ ID NO 2
<211> LENGTH: 32
<212> TYPE: DNA
<213> ORGANISM: Artificial sequence
<220> FEATURE:
<223> OTHER INFORMATION: Upstream primer

<400> SEQUENCE: 2
taggatcccg atgattaagc attttcattt ta                                 32

<210> SEQ ID NO 3
<211> LENGTH: 33
<212> TYPE: DNA
<213> ORGANISM: Artificial sequence
<220> FEATURE:
<223> OTHER INFORMATION: Downstream primer

<400> SEQUENCE: 3
tagaattcgc ctgaccgaag acaatgactt att                                33

<210> SEQ ID NO 4
<211> LENGTH: 21
<212> TYPE: PRT
<213> ORGANISM: Artificial sequence
<220> FEATURE:
<223> OTHER INFORMATION: Microcin J25

<400> SEQUENCE: 4

Gly Gly Ala Gly His Val Pro Glu Tyr Phe Val Gly Ile Gly Thr Pro
1               5                   10                  15

Ile Ser Phe Tyr Gly
            20
```

RECOMBINANT ESCHERICHIA COLI AND APPLICATION OF THE SAME

TECHNICAL FIELDS

The invention relates to a genetic engineering strain and application thereof. Particularly, the invention relates to a recombinant *Escherichia coli* with high yield of Microcin J25 and application thereof.

BACKGROUND TECHNOLOGY

The problem of bacterial resistance caused by excessive use of antibiotics has become increasingly prominent, putting clinical anti-infective treatment into trouble. In the aquaculture industry, the long-term use of antibiotic growth-promoting agents is more serious. In addition, the large amount of antibiotic residues not only indirectly causes harm to human health, but also causes low immunity of livestock and poultry, increasing the incidence of infectious diseases, and increasing the cost of breeding. Grain-negative bacteria such as *Escherichia coli* and Salmonella are prone to drug resistance, and the diseases caused by them cause huge losses to animal husbandry. Therefore, there is an urgent need to solve this problem.

Antimicrobial peptides (AMPs) are the oldest anti-microbial infection polypeptides in biological evolution. They are also an important component of innate immune regulation from prokaryotes to humans. They are inherent immune effector molecule in direct antibacterial and microbial regulation. The current research shows that antibacterial peptides are active in broad-spectrum antibacterial, anti-viral, anti-tumor, anti-protozoal, immunity regulation, and are not susceptible to drug resistance.

Microcin J25 obtained by fermentation, separation and purification of *Escherichia coli* modified by genetic engineering is one kind of antibacterial peptide. Vitro bacteriostatic tests showed that Microcin J25 is able to kill a variety of pathogenic *E. coli* and Salmonella. It is currently believed that Microcin J25 inhibits pathogenic microorganisms mainly by the following two methods: first, interfering with bacterial mRNA and protein synthesis by inhibiting RNA polymerase activity, second, changing the permeability of the cell membrane rather than breaking the bacterial cell membrane such that the contents are extravasated and the pathogenic bacteria are killed. The mature Microcin J25 is a lasso peptide consisting of 21 amino acids, in which the first amino acid to the eighth amino acid of the N-terminus form a circular ring structure, and the ninth amino acid to the 21 amino acid form a hairpin structure which penetrates the circular ring structure and fixes the tail by non-covalent action. In theory, the structure is very stable in physical and chemical properties, can resist strong denaturing conditions, and has good tolerance to temperature, protease, acid and alkali, etc. It has been proved by experiments that Microcin J25 can withstand high temperature and high pressure of 121° C., and it is still active after gastrointestinal fluid treatment simulation. It can be seen that Microcin J25 is suitable for industrial scale production and can take effect by reaching the end of animal intestine. However, there have been no reports of industrial production of Microcin J25.

TECHNICAL CONTENTS

Technical Purpose

The technical object of the present invention is to provide a recombinant *Escherichia coli* with high yield of Microcin J25 and its application.

Technical Solutions

In one aspect, the present invention provides a recombinant *Escherichia coli* ZH021802, which is deposited on Aug. 28, 2018 in the China General Microbiological Culture Collection Center (CGMCC, Address: Building 3, No. 1, Beichen West Road, Chaoyang District, Beijing, Institute of Microbiology, Chinese Academy of Sciences, Zip Code 100101), with the preservation number CGMCC No. 16349.

In an embodiment of the present invention, the recombinant *Escherichia coli* ZH021802 is subjected to fermentation culture, and the concentration of Microcin J25 in the supernatant may reach 4000 mg/L or more.

In another aspect, the invention provides the use of the above recombinant *Escherichia coli* ZH021802 for the production of Microcin J25.

In still another aspect, the present invention provides a method of preparing Microcin J25, characterized in that Microcin J25 is obtained by fermentating the above recombinant *Escherichia coli* ZH021802.

TECHNICAL EFFECT

Compared with the recombinant *Escherichia coli* expressing Microcin J25 in the prior art, the recombinant *Escherichia coli* according to the present invention can greatly improve the expression level of Microcin J25, and is suitable for industrial production of Microcin J25.

SPECIFIC IMPLEMENTATION

Figure 1:
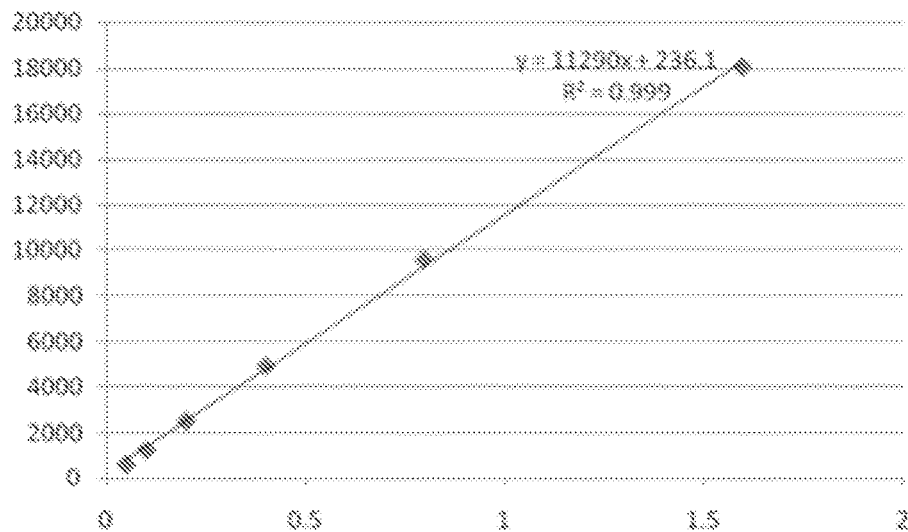
FIG. 1 is a standard curve for determining the concentration of Microcin J25 prepared in Preparation Example 4.

The following embodiments are merely illustrative examples of the present invention and are intended to make a person skilled in the art better understand the invention rather than limit the scope of the invention.

Experimental Materials

Templates and Strains

The DNA template for expression of Microcin J25 by *Escherichia coli* was provided by Zhengzhou Zhongsheng Biotechnology Co., Ltd. (for the full sequence, please see SEQ ID No.: 1 in the Sequence list).

*Escherichia coli* BL21 competent cells (item number: CD901-03, supplier: Beijing Transgen Biotech Co., Ltd.).

*Escherichia coli* MC4100 (purchased from (China Center of Industrial Culture Collection (CICC)).

Vector

The pMD18-T cloning vector and the pGEX-6p-1 expression vector were products of Invitrogen Company.

Preparation of PCR Amplification of the Target Gene Fragment of Example 1

1. The full sequence of the target gene mcjABCD fragment (see sequence list SEQ ID No.: 1)
2. The primers used are as follows (the Restriction Enzyme cutting sites are underlined):

```
Upstream primer:
                                    (SEQ ID No.: 2)
TAGGATCCCGATGATTAAGCATTTTCATTTTA Downstream primer:
                                    (SEQ ID No.: 3)
TAGAATTCGCCTGACCGAAGACAATGACTTATT
```

3. PCR reaction system and reaction conditions

TABLE 1

| PCR Reaction System | |
| --- | --- |
| Components | Dosage |
| dd H$_2$O | 36.7 μl |
| 5% DMSO | 2.5 μl |
| 10 × Buffer | 5 μl |
| upstream primer | 1 μl |
| downstream primer | 1 μl |
| dNTPs | 1 μl |
| DNA Template | 2 μl |
| TaqE (5 U/μl) | 0.8 μl |
| Total | 50 μl |

TABLE 2

| PCR Reaction Conditions | | |
| --- | --- | --- |
| Step | Temperature | Time |
| denaturalization | 97° C. | 1 min |
| 15 cycles | 94° C. | 1 min |
| | 55° C. | 1 min |
| | 72° C. | 1 min |
| 20 cycles | 94° C. | 1 min |
| | 55° C. | 1 min |
| | 72° C. | 1.5 min |
| keep | 4° C. | +∞ |

Preparation of Example 2 Connection of the Fragment of Interest to pMD18-T Vector and Plasmid Transformation 1. The enzyme reaction system is shown in Table 3 below.

TABLE 3

| Components | Dosage |
| --- | --- |
| dd H$_2$O | 13.5 μl |
| 10 × T4 DNA Ligase Buffer | 2 μl |
| pMD18-T vector | 0.5 μl |
| DNA | 3 μl |
| T4 DNA Ligase | 1 μl |
| Total | 20 μl |

The above components were mixed and centrifuged briefly, and the prepared system was allowed to stand at 16° C. overnight. The connected system was placed in a refrigerator at 4° C. for use.

2. Heat Shock Plasmid Transformation a. The prepared 100 μl of *E. coli* BL21 competent cells was taken from a freezer at −80° C., was placed on ice for 10 min, and kept in a 0° C. state. In the clean bench, 10 μl of the corresponding enzyme-linked product (pMD18-T vector connected with the target gene mcjABCD fragment prepared above) was separately added to the competent cells, and the contents were gently rotated and mixed, and placed on ice for 30 min (In the test, DNA without plasmid can be set as a comparison);

b. Heat shock: The temperature of the water bath pot was accurately adjusted to 42° C. with a thermometer, and the sample was taken out and placed in a 42° C. water bath for accurate heat shock for 90 s;

c. Iced: The EP tube quickly is taken out of the ice and the cells is cooled for 2 min;

d. Resuscitation: 400 μl of LB medium that had been preheated in a 37° C. incubator was added into the EP tube and incubated for 1.5 h at 180°/min on a 37° C. shaker to resuscitate the bacteria;

e. Cloth: In the clean bench, the 300 μl and 150 μl of the transformed competent cells were taken to be transferred to a plate, respectively, and were uniformly coated onto the surface of an agar plate with a sterile elbow glass rod;

f. Culture: The plate was placed in a 37° C. incubator for positive incubation until the liquid was absorbed, then inverted for culture, and colonies appear after 12-16 hours.

g. MasterPlate: The overnight cultured plate was taken out. In the clean bench, 10 single colonies from each plate were picked for streak culture in two solid LB culture plates with a diameter of 15 cm for monoclonal expansion and further screening. The picked colonies were numbered 1-10, and cultured in a 37° C. incubator for 12 hours.

Preparation Example 3 Double Digestion (BamHI and EcoR I) Plasmid and Expression Vector pGEX-6p-1 and Connection Thereof 1. A mixture of enzyme digestion systems for digestion of the plasmid and expression vector were prepared, and then dispensed to each 0.6 ml EP tube. The final enzyme digestion system (Takara) of each tube is shown in Table 4 below.

TABLE 4

| components | dosage |
| --- | --- |
| ddH$_2$O | 30 μl |
| 10 × Proteinase K Buffer | 4 μl |
| BamH I | 1 μl |
| EcoR I | 1 μl |
| plasmid | 4 μl |
| Total | 40 μl |

The enzyme was digested in a 37° C. incubator for no more than 1.5 h, and 2 μl of 10×Buffer was added to terminate the digestion. The results showed that the enzyme digestion effect was good. The target fragment was recovered by the plasmid which was digested with the same step, and the expression vector after digestion was placed in a refrigerator at 4° C. for use.

2. The resulting fragment was recovered and connected to the pGEX-6p-1 expression vector.

The enzyme-linked reaction system was prepared as shown in Table 5 below.

TABLE 5

| Components | Dosage |
| --- | --- |
| ddH$_2$O | 13.5 μl |
| 10 × T4 DAN Ligase Buffer | 2 μl |
| pGEX-6p-1 | 0.5 μl |
| DNA | 3 μl |
| T4 DNA Ligase | 1 μl |
| Total | 20 μl |

After mixed, the mixture was briefly centrifuged, and the prepared system was allowed to stand at 16° C. for overnight. The connected system was placed in a refrigerator at 4° C. for use.

3. Heat shock plasmid transformation

The recombinant plasmid was transformed into the expression host of *Escherichia coli* MC4100 (purchased from China Center of Industrial Culture Collection (CICC) by heat-shocking (specifical operations are the same as those in Preparation Example 2 above), and the transformed *Escherichia coli* MC4100 cells were collected. The plate was applied to an LB medium (10 g of tryptone, 5 g of yeast extract, 10 g of NaCl, and 15 g of agar were dissolved in purified water and made up to 1 L with purified water), and cultured at 37° C. until the appearance of a single colony. After the transformants were verified by plasmid extraction and PCR, the next step of culture and fermentation was carried out.

Preparation Example 4 Culture of Recombinant *Escherichia Coli* Transformants

Four transformant single colonies and one *Escherichia coli* MC4100 single colony were picked and inoculated separately into 25 ml of liquid medium (32 g of corn flour, 20 g of soybean meal, 13 g of peptone, 15 g of glucose, 2 g of KH2PO4 and 1.20 g of ammonium sulfate were dissolved in purified water and made up to 1 L with purified water), and were shaken at 37° C., 200 rpm for 12-18 h, centrifuged at 10,000 rpm for 10 min, and the supernatant was collected. The concentration of the target polypeptide Microcin J25 in the supernatant was determined by high performance liquid chromatography.

High performance liquid chromatography conditions are as follows:

Using octadecylsilane bonded silica as a filler (high performance liquid chromatography: Agilent 1260, C18 column: ZORBAX 300SB-C18, 5 μm, 4.6×250 mm), with trifluoroacetic acid-water-acetonitrile (1:950:50) for mobile phase A, with trifluoroacetic acid-water-acetonitrile (0.85:100:900) as mobile phase B, column temperature 25° C., detection wavelength 214 nm, flow rate 1 ml/min, injection volume 10 μL, Gradient elution is conducted as shown in Table 6 below. The number of theoretical plates is not less than 2000 according to the peak of Microcin J25.

TABLE 6

| Time (Min) | A (%) | B (%) |
| --- | --- | --- |
| 0 | 80 | 20 |
| 20 | 60 | 40 |

TABLE 6-continued

| Time (Min) | A (%) | B (%) |
| --- | --- | --- |
| 20.01 | 0 | 100 |
| 30 | 0 | 100 |
| 30.01 | 90 | 10 |
| 36 | 90 | 10 |

The peak position of Microcin J25 standard is 12 min-13.5 min. The standard curve of peak area and Microcin J25 concentration is shown in FIG. 1. The standard curve equation is y=11290x+236.1 (x is the standard concentration, the unit is mg/ml, y For the average peak area).

The concentrations of Microcin J25 in the supernatant obtained from the four transformed strains were 3560 mg/L, 3720 mg/L, 3610 mg/L and 4200 mg/L, respectively, whereas the concentration of Microcin J25 in the supernatant obtained from *E. coli* MC4100 was 270 mg/L. Therefore, the *Escherichia coli* constructed by the present invention has a high level of ability to express Microcin J25.

The *Escherichia coli* genetically engineered strain with the highest yield of Microcin J25 was named as *Escherichia coli* ZH021802. The *Escherichia coli* ZH021802 was deposited on Aug. 28, 2018 in the (China General Microbiological Culture Collection Center, (CGMCC, Address: Building 3, No. 1 Beichen West Road, Chaoyang District, Beijing, China, Institute of Microbiology, Chinese Academy of Sciences, Zip Code) 100101), the preservation number is CGMCC No. 16349.

Experimental Example 1 The Structure of the Expression Product Microcin J25 was Verified by Mass Spectrometry Test instrument name and model: electrospray tandem mass spectrometer micrOTOF-Q II (Bruker)

Test sample: a pure product of Microcin J25 obtained from the fermented *Escherichia coli* ZH021802 in the above Preparation Example 4

Test results: See Table 7.

TABLE 7

| Microcin J25 before and after reduction | | | | |
| --- | --- | --- | --- | --- |
| Sample | Actual Measurement Molecular weight (Da) | Theory Molecular weight (Da) | Relative Deviation (%) | Notes |
| Microcin J25 | 2105.9970 | 2106.0210 | −0.0011 | Target Peptides |

Conclusion: The exact molecular weight of Microcin J25 was determined by LC-MTQ-MS. The results showed that the measured molecular weight was 2105.9970 Da, and the relative deviation from the theoretical molecular weight was −0.0011%. The molecular weight of the sample shown in this test is basically the same as the molecular weight 2.1 kDa of Microcin J25 reported in literature [1] (Marvin J. Bayro et al., "Structure of antibacterial peptide microcin J25: A 21-residue lariat protoknot", J. AM. CHEM. SOC. Vol. 125, No. 41 Period, Pages 12382-12383, 2003). Therefore, it can be seen that this sample has structural information to Microcin J25.

Experimental Example 2 Amino Acid Sequencing of the Expression Product Microcin J25

Test instrument name and model: electrospray tandem mass spectrometer micrOTOF-Q II (Bruker), high performance liquid chromatography HPLC1100 (Agilent)

Test sample: *Escherichia coli* ZH021802 obtained in the above Preparation Example 4 was fermented to obtain a pure product of Microcin J25.

Test results:

G1-G2-A3-G4-H5-V6-P7-E8-Y9-F10-V11-G12-I13-G14-T15-P16-I17-S18-F 19-Y20-G21

(SEQ ID No.: 4 in the sequence list)

The amino acid sequence of the sample shown in this test is completely consistent with the amino acid sequence of Microcin J25 reported in the literature [1]. It can be seen that this sample has structural information corresponding to Microcin J25.

Experimental Example 3 Detection of Secondary Structure of the Expressed Product Microcin J25

Name and Model of Measurement Instrument: Pistar π-180 Circular Dichroism Spectroscopy (Applied Photophysics Ltd).

Test Sample: A pure product of Microcin J25 of fermented *Escherichia coli* ZH021802 obtained in the above Preparation Example 4

Figure 2:
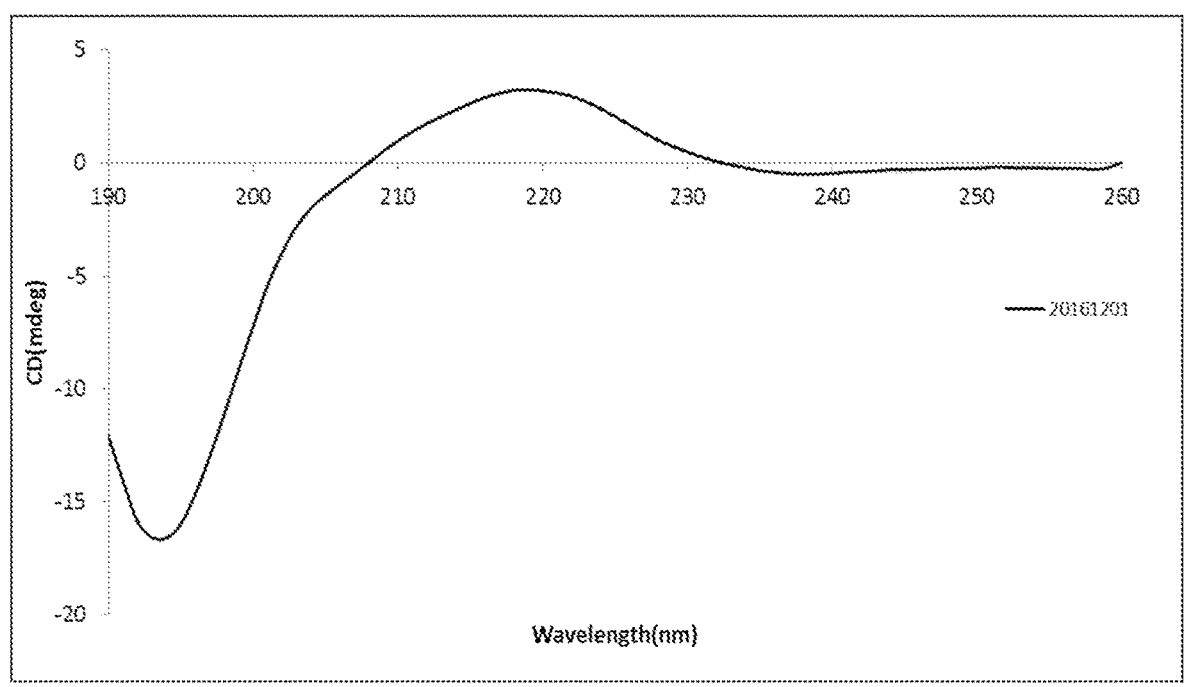
FIG. 2 is a test chart of Microcin J25 prepared by preparing a binary dichroism test of Example 4.

Test results: The test pattern is shown in FIG. 2.

The results of the analysis are shown in Table 8 below.

TABLE 8

| Microcin J25 ratio of the secondary structure (190 nm~260 nm) | | | | | |
|---|---|---|---|---|---|
| Batch No. | α-spiral (%) | β-folded (%) | β-turning (%) | random coil (%) | unitary mismatch (%) |
| Microcin J25 | 4.5 | 29.1 | 18.6 | 47.8 | 0.030 |

---

The invention claimed is:

1. A recombinant *Escherichia coli* ZH021802, deposited on Aug. 28, 2018, in the General Microbiology Center of the China Microbial Culture Collection Management Committee, with the preservation number CGMCC No. 16349.

2. A method for preparing Microcin J25, wherein Microcin J25 is produced by fermentation of the recombinant *Escherichia coli* ZH021802 according to claim 1.

* * * * *